United States Patent [19]

Caldarise et al.

[11] Patent Number: 5,201,767
[45] Date of Patent: Apr. 13, 1993

[54] FLUTED-WEDGE OSTEAL PROSTHETIC COMPONENT

[75] Inventors: Salvatore Caldarise, Hanson; Thomas S. Thornhill, Dover, both of Mass.

[73] Assignee: Johnson & Johnson Orthopaedics, Inc., Raynham, Mass.

[21] Appl. No.: 729,674

[22] Filed: Jul. 15, 1991

[51] Int. Cl.$^5$ .......................... A61F 2/30; A61F 2/32; A61F 2/36
[52] U.S. Cl. .................................. 623/18; 623/16; 623/22; 623/23
[58] Field of Search .................. 623/16, 18, 20, 22, 623/23

[56] References Cited

U.S. PATENT DOCUMENTS

| | | | |
|---|---|---|---|
| 2,719,522 | 10/1955 | Hudack | 623/23 |
| 3,906,550 | 9/1975 | Rostoker et al. | 623/22 |
| 3,987,499 | 10/1976 | Scharbach et al. | 623/22 X |
| 4,430,761 | 2/1984 | Niederer et al. | 623/18 |
| 4,549,319 | 10/1985 | Meyer | 623/22 |
| 4,623,349 | 11/1986 | Lord | 623/18 |
| 4,661,112 | 4/1987 | Muller | 623/22 |
| 4,728,334 | 3/1988 | Spotorno | 623/23 |
| 4,883,488 | 11/1989 | Bloebaum | 623/20 |
| 4,936,863 | 6/1990 | Hofmann | 623/23 |
| 4,944,759 | 7/1990 | Mallory et al. | 623/23 X |
| 4,944,761 | 7/1990 | Stuhmer et al. | 623/23 |

FOREIGN PATENT DOCUMENTS

| | | | |
|---|---|---|---|
| 2528307 | 12/1983 | France | 623/23 |
| 2639821 | 6/1990 | France | 623/22 |

OTHER PUBLICATIONS

Harris et al., 15th Ann. Meeting of the Society for Biomaterials, p. 60 (1989).
Whiteside Brochure (1985).

*Primary Examiner*—Ronald Frinks
*Attorney, Agent, or Firm*—Hamilton, Brook, Smith & Reynolds

[57] ABSTRACT

An osteal prosthetic component of a prosthetic joint and a method of implanting an osteal prosthetic component in the medullary canal of a bone are disclosed. The osteal prosthetic component includes a stem for disposition within a medullary canal of a bone and a fluted wedge portion extending from the stem. The fluted wedge has wedge portions which define at least one flute between the wedge portions. An interference fit is formed between the wedge portions and the bone during implantation of the stem into the medullary canal. Movement of the osteal prosthetic component relative to the bone is thereby sufficiently limited to allow tissue growth into a tissue-ingrowth portion at the surface of the stem to substantially prevent micromotion of the stem relative to the bone.

10 Claims, 3 Drawing Sheets

FLUTED-WEDGE OSTEAL PROSTHETIC COMPONENT

Prosthetic bone joints, such as prosthetic hips, often include a component which is implanted in a medullary canal of a bone. However, motion of prosthetic bone joints relative to bone in which they are implanted, such as by pistoning or by rotation, can cause pain and diminish their utility. Further, the useful life of prosthetic bone joints can be significantly reduced by such motion, thereby requiring surgery to reconstruct or replace the joint.

One method of limiting movement of the component includes cementing the stem to the bone. However, cement can deteriorate over prolonged periods of time, thereby causing failure of the bond between the stem and the bone and consequent loosening of the prosthetic bone joint. In addition, tissue in which the prosthetic bone joint has been implanted can develop an adverse reaction to cement.

In another method, porous surface portions are formed on the osteal prosthetic stem to allow tissue to grow into the porous surface portions and thereby fix the stem to the bone. However, even micromotion of the prosthesis relative to the bone during bony ingrowth, i.e. in the range of between about two hundred and about three hundred microns, typically limits the amount of bony ingrowth into porous surface portions. The stem can thereby remain loose within the medullary canal of the bone in which it has been implanted, causing pain in tissue surrounding the prosthetic bone joint and significantly reducing use of the prosthetic bone joint.

Therefore, a need exists for a new component of a prosthetic joint which overcomes or minimizes the above-mentioned problems.

SUMMARY OF THE INVENTION

The present invention relates to a new osteal prosthetic component of a prosthetic joint for disposition within a medullary canal of a bone.

An osteal prosthetic component of a prosthetic joint for disposition within a medullary canal of a bone includes a neck and a stem extending from the neck. The stem includes a tissue-ingrowth portion for allowing tissue growth from the bone into the stem to substantially prevent micromotion of the stem relative to the bone. A fluted wedge portion extends from the stem and includes wedge portions which define at least one flute between the wedge portions, whereby an interference fit is formed between the wedge portions and the bone during implantation of the stem into the medullary canal, thereby sufficiently limiting movement of the stem relative to the bone to allow tissue growth at the tissue-ingrowth portion to substantially prevent micromotion of the shank relative to the bone.

A method of implanting an osteal prosthetic component of a prosthetic joint in a medullary canal of a bone includes directing a stem of the osteal prosthetic component into a medullary canal of a bone, whereby an interference fit is formed between the bone and wedge portions of a fluted wedge portion of the stem. Movement of the stem is thereby sufficiently limited relative to the bone to allow tissue growth from the bone into a tissue-ingrowth portion of the stem to substantially prevent micromotion of the stem relative to the bone.

This invention has many advantages. In general, an interference fit is formed between the wedge portions of the fluted wedge and the bone by implantation of the osteal prosthetic component of the prosthetic joint into a medullary canal of the bone. The interference fit sufficiently limits relative motion between the stem and the bone, such as axial and rotational movement of the stem within the bone, to allow tissue growth into a tissue-ingrowth portion of the stem. The tissue growth into the tissue-ingrowth portion fixes the stem to the bone and substantially prevents micromotion of the stem relative to the bone. Pain in surrounding tissue associated with motion of the component relative to bone in which it is implanted is thereby significantly reduced and the utility of the osteal prosthetic joint is significantly increased. Also, longevity of useful function of the prosthesis is improved.

BRIEF DESCRIPTION OF THE INVENTION

DETAILED DESCRIPTION OF THE INVENTION

The features and other details of the apparatus and method of the invention will now be more particularly described with reference to the accompanying drawings and pointed out in the claims. The same number present in different figures represents the same item. It will be understood that the particular embodiments of the invention are shown by way of illustration and not as limitations of the invention. The principle features of this invention can be employed in various embodiments without departing from the scope of the invention.

Figure 1:
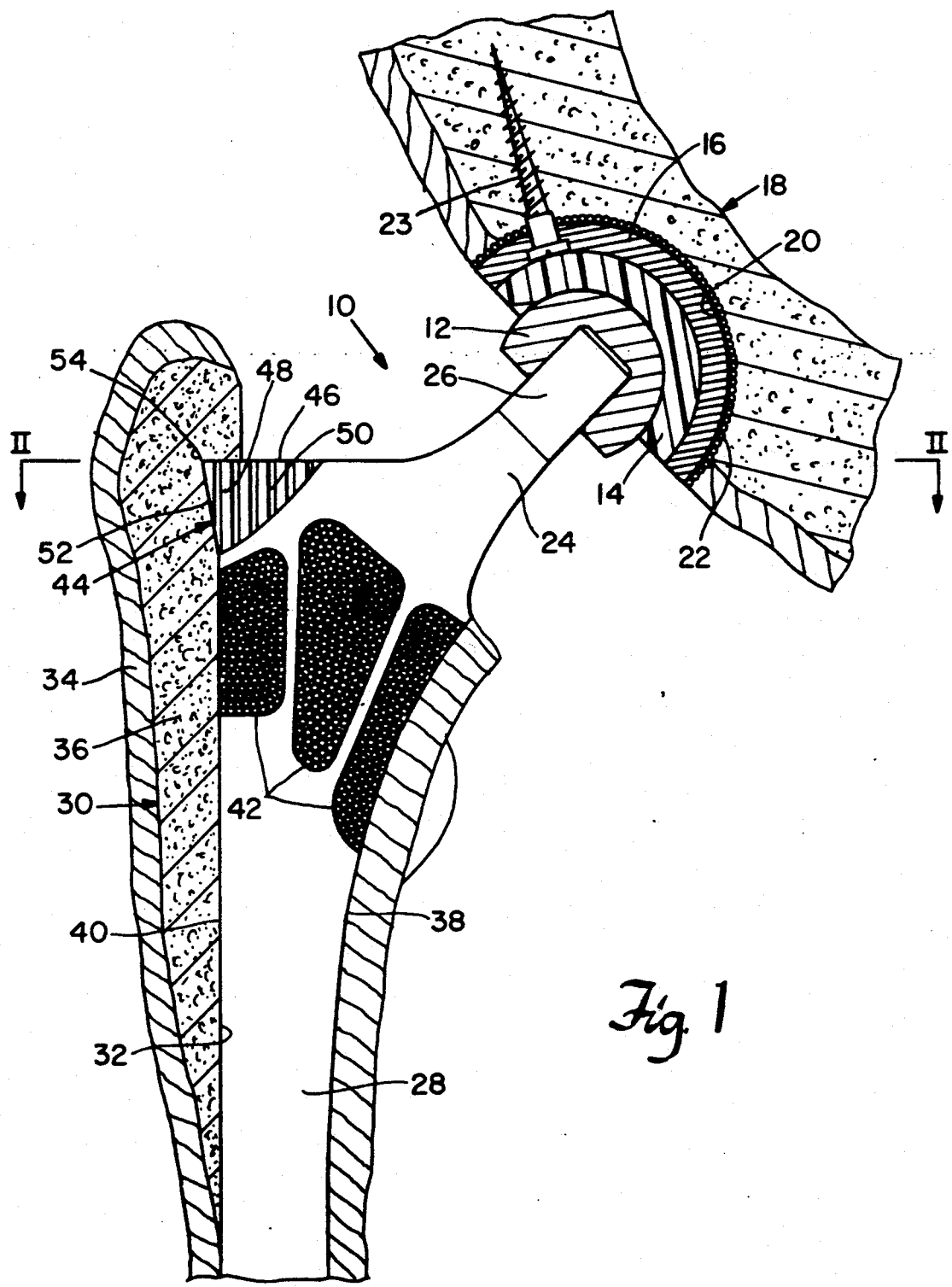
FIG. 1 is side view of a prosthetic joint, including an osteal prosthetic component according to the invention, which has been implanted in the medullary canal of a femur.

In one illustration of the invention, shown in FIG. 1, osteal prosthetic component 10 is mounted in femoral head 12. Femoral head 12 is disposed in liner 14. Femoral head 12 is rotatable within liner 14 for movement of osteal prosthetic component 10. Liner 14 is disposed in cup 16. Acetabulum 18 defines recessed portion 20. Cup 16 is disposed within recessed portion 20. Surface portion 22 of cup 16 abuts acetabulum 18 at recessed portion 20. Surface portion 22 is suitable for fixation of cup 16 to acetabulum 18 by bone tissue growth at surface portion 22. Screw 23 extends through cup 16 into acetabulum 18 at recessed portion 20 for anchoring cup 16 in recessed portion during fixation of cup in acetabulum 18 by tissue growth at surface portion 22.

Osteal prosthetic component 10 includes neck 24. Pin 26 extends from neck 24 and is disposed within femoral head 12. Alternatively, femoral head 12 and neck 24 can be intergral. Stem 28 extends from neck 24. Stem 28 is disposed within femur 30 by implantation of stem 28 within medullary canal 32 of femur 30.

Stem 28 abuts cortical tissue 34 and cancellous tissue 36 of femur 30. Stem 28 includes medial side 38, which is located inferiorly to femoral head 12, and a lateral side 40, which is located on the opposite side of stem 28 to medial side 38. Tissue-ingrowth portions 42 are disposed at stem 28 inferior to neck 24. Tissue-ingrowth portions 42 are suitable for allowing tissue growth, such as bone tissue growth, into tissue-ingrowth portions 42 to thereby substantially prevent micromotion of stem 28 relative to femur 30. Relative motion between stem 28 and femur 30 includes, for example, piston-like movement along a line parallel to the major axis of stem 28 and also rotational movement of stem 28 about a major axis of stem 28. "Micromotion," as that term is used herein, means relative motion in the range of between about two hundred and about three hundred microns.

An example of suitable tissue-ingrowth portions 42 include cobalt/chromium beads fixed to stem 28, such as is known in the art. In one embodiment, the beads have a diameter in the range of between about 0.5 millimeters and about 0.75 millimeters. The depth of the beads at shank 28 is in the range of between about one millimeter and about 1.5 millimeters. The beads form pores having an average diameter in the range of between about two hundred and eighty and about three hundred microns.

Fluted wedge 44 is a segment of a right circular cone having a base 46 extending from stem 28 at a point along lateral side 40 most proximate to neck 24. Base 46 extends generally transversely to a longitudinal axis of stem 28. Fluted wedge 44 includes wedge portions 48 which define flutes 50, disposed between wedge portions 48. Wedge portions 48 each include a ramp surface 52 and a rim 54 disposed between ramp surface 52 and base 46. Ramp surface 52 extends generally along the longitudinal axis of stem 28. Ramp surface 52 and base 46 of each wedge portion 48 intersect to form rim 54 of each wedge portion 48. Ramp surface 52 is a portion of the outer surface of the right circular cone segment. Rim 54 is a portion of the directrix at the base of the right circular cone segment. It is to be understood, however, that fluted wedge 44 can be configured as a segment of a cone-like shape wherein, for example, the generator of the conic segment is not straight.

Osteal prosthetic component 10, including pin 26, neck 24 and stem 28, are formed of a suitable material for implanting in a bone. Examples of suitable materials include metallic alloys of titanium, cobalt and chromium, as well as composites of these metals and alloys. Preferred materials include, for example, TI-6Al-4V alloy and Co-Cr alloys.

Figure 2:
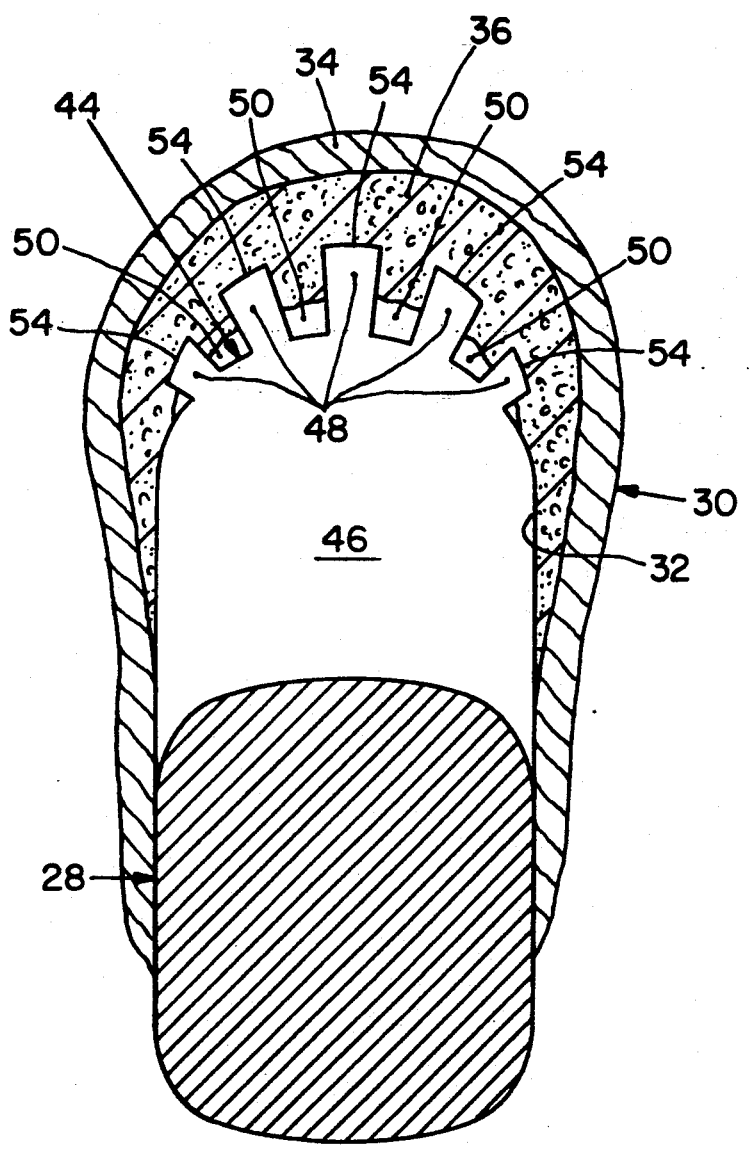
FIG. 2 is a partial section view of the osteal prosthetic component illustrated in FIG. 1 taken along line II—II.

As illustrated in FIG. 2, wedge portions 48 extend radially from stem 28. Rims 54 at wedge portions 48 outline base 46. Wedge portions 48 extend substantially parallel to a major axis of stem 28. The number of wedge portions 48 of fluted wedge 44 is sufficient to cause an interference fit between wedges 48 and femur 30 during implantation of osteal prosthetic stem 10 in medullary canal 32. The interference fit sufficiently limits motion of stem 28 within medullary canal 32 to allow tissue ingrowth into the tissue-ingrowth portions of stem 28 which, in turn, will prevent micromotion of stem 28 relative to femur 30. Preferably, the number of flutes 50 is in the range of from about seven and to about nine.

The diameter of base 46 of fluted wedge 44 is sufficient to cause an interference fit between wedges 48 and femur 30 and stem 28 which will allow sufficient tissue ingrowth into the tissue-ingrowth portions of stem 28 to prevent micromotion of stem 28 relative to femur 30. In one embodiment, the diameter of base 46 of fluted wedge 44 is oversized for the space formed in medullary canal 32 by reeming, while the diameter of stem 28 is a line-to-line fit with the space formed. Preferably, the diameter of base 46 is oversized by about one millimeter.

Typically, the radius of base 46 is in the range of between about 0.296 inches and about 0.482 inches, the width of wedges 48 is in the range of between about 0.050 inches and about 0.150 inches, and the width of flutes 50 is in the range of between about 0.040 inches and about 0.060 inches. In a particularly preferred embodiment the width of flutes 50 is about 0.097 inches.

Figure 3:
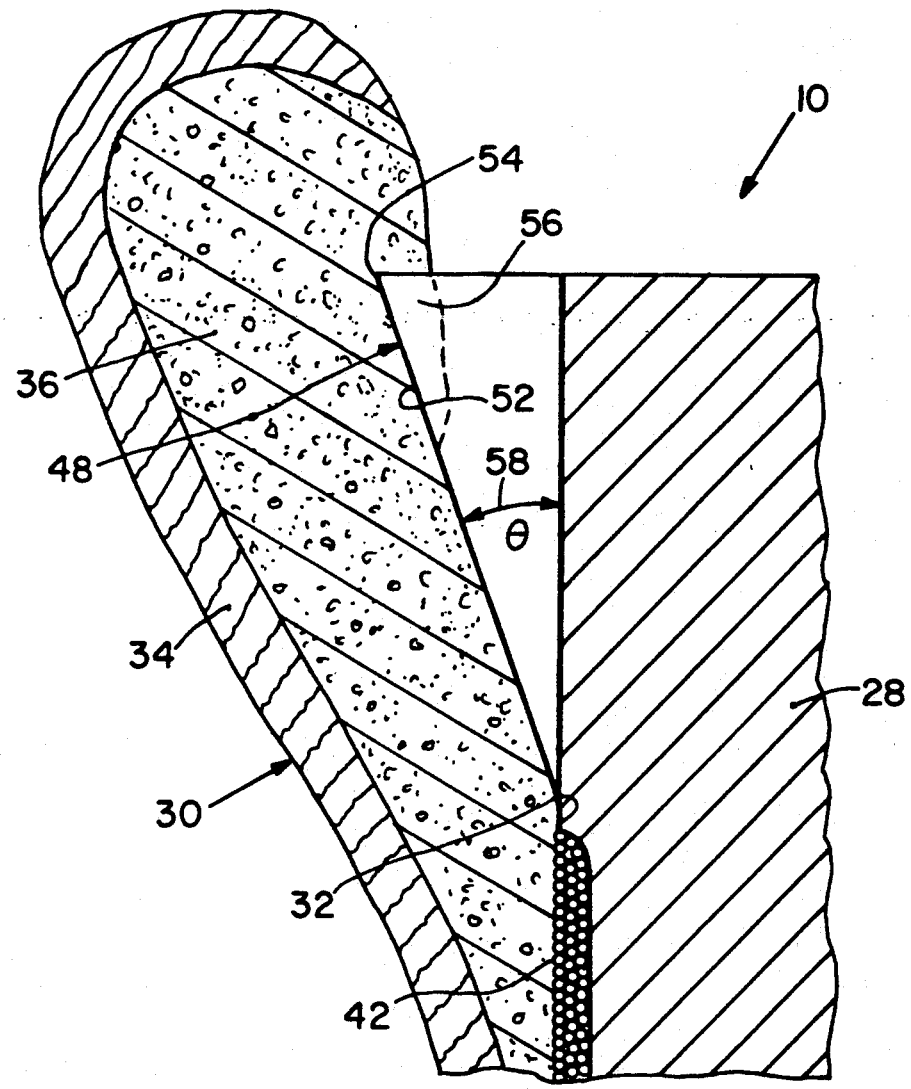
FIG. 3 is a section view, partly broken away, of a fluted wedge of the osteal prosthetic component illustrated in FIG. 1.

As can be seen in FIG. 3, implantation of osteal prosthetic component 10 in medullary canal 32 of femur 30 directs ramp surface 52 against femur 30. Continued direction of osteal prosthetic component 10 into medullary canal 32 directs rim 54 into femur 30 bone tissue. A portion of the bone tissue 56 (shown in phantom) is directed by wedge portions 48 into the flutes between wedge portions 48. An interference fit is thereby formed between fluted wedge 44 and femur 30. The interference fit can cause contact of ramp surface 52 and base 46 with bone tissue of femur 30.

The interference fit formed between wedge portions 48 and femur 30 is sufficient to limit movement of stem 28 relative to femur 30 to a range of movement which is sufficiently small to allow tissue ingrowth from femur 30 into tissue-ingrowth portions 42, thereby substantially preventing micromotion of stem 28 relative to femur 30.

Ramp surface 52 extends from the major axis of stem 28 at an angle H 58 to the major axis which allows implantation of osteal prosthetic component 10 in medullary canal 32 without significant damage to femur 30. In one embodiment, angle H 58 of ramp surface 52 to the major axis of stem 28 is in the range of between about 17° and about 13°.

Following implantation of osteal prosthetic component 10 in medullary canal 32 of femur 30, tissue of femur 30 adjacent to tissue-ingrowth portions 42 grow into the pores at tissue-ingrowth portions 42. The amount of tissue growth into tissue-ingrowth portions 42 is sufficient to prevent micromotion of stem 28 relative to femur 30. Also, tissue ingrowth into tissue-ingrowth portions 42 fix osteal prosthetic component 10 to femur 30.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

We claim:

1. An osteal prosthetic component of a prosthetic joint for disposition within a medullary canal of a bone, comprising:
   a) a neck:
   b) a stem extending from the neck along a longitudinal axis, the stem including a tissue ingrowth portion for allowing bone tissue growth from the bone into the stem to substantially prevent micromotion of the stem relative to the bone; and
   c) fluted wedge extending from the stem, the fluted wedge having wedge portions which define at least one flute between the portions, each wedge portion including a ramp, which extends generally along the longitudinal axis, and a base portion extending generally transversely to said longitudinal axis, the ramp and the base portion intersecting to form a rim, whereby an interference fit is formed between the rims and the bone during implantation of the stem into the medullary canal, wherein the interference fit can cause contact of at least a portion of the ramps and the base portions with the bone, thereby sufficiently limiting the movement of the stem relative to the bone to allow tissue growth at the tissue-ingrowth portion to substantially prevent micromotion of the stem relative to the bone.

2. An osteal prosthetic component of claim 1 wherein the fluted wedge is disposed at a lateral portion of the stem inferior to the neck, and wherein the wedge portions are substantially parallel to a major axis of the stem.

3. An osteal prosthetic component of claim 2 wherein the fluted wedge is configured as a segment of a right circular cone.

4. An osteal prosthetic component of claim 3 wherein the wedge portions extend radially from a major axis of the right circular cone.

5. An osteal prosthetic component of claim 4 wherein the base of the right circular cone has a radius in the range of between about 0.296 and about 0.482 inches.

6. An osteal prosthetic component of claim 5 wherein the height of the right circular cone is in the range of between about 0.460 and about 0.620 inches.

7. An osteal prosthetic component of claim 6 wherein the individual wedge portions of the cone have a width in the range of between about 0.050 and about 0.150 inches.

8. An osteal prosthetic component of claim 7 wherein the number of flutes between the wedge portions is in the range of from seven to nine.

9. A method of implanting an osteal prosthetic component of a prosthetic joint in a bone, comprising the step of directing a stem which extends from a neck of the osteal prosthetic component along a longitudinal axis, in a medullary canal of the bone, whereby an interference fit is formed between the bone and rims of wedge portions of a fluted wedge of the osteal prosthetic component, the wedge portions defining at least one flute between the wedge portions, each wedge portion including a ramp, which extends generally along the longitudinal axis, and a base portion extending generally transversely to said longitudinal axis, the ramp and the base portion of each wedge portion intersecting to form a rim, whereby an interference fit is formed between the bone and the rims of the osteal prosthetic component, wherein the interference fit causes contact of at least a portion of the ramps and the base portions with the bone, thereby sufficiently limiting movement of the stem relative to the bone to allow tissue growth from the bone into a tissue-ingrowth portion of the stem to substantially prevent micromotion of the stem relative to the bone.

10. In a component of a prosthetic joint for disposition within a medullary canal of a bone, the component including a neck and a stem extending from the neck along a longitudinal axis, wherein the stem has a tissue-ingrowth portion for allowing bone tissue growth form the bone into the stem to fix the component to the bone:

the improvement comprising a fluted wedge extending from the stem, the fluted wedge portion having wedge portions which define at least one flute between the wedge portions, each wedge portion including a ramp, which extends generally along the longitudinally axis, and a base portion extending generally transversely to said longitudinal axis, the ramp and the base portion of each wedge portion intersecting to form a rim, whereby an interference fit is formed between the rims and the bone during implantation of the component into the medullary canal, wherein the interference fit can cause contact of at least a portion of the ramps and the base portions with the bone, thereby sufficiently limiting movement of the stem relative to the bone to allow tissue growth at the tissue-ingrowth portion to substantially prevent micromotion of the stem relative to the bone.

* * * * *